United States Patent [19]

Isaac et al.

[11] 3,932,533
[45] Jan. 13, 1976

[54] PROCESS FOR THE RECOVERY OF PURE ALPHA-BISABOLOL

[75] Inventors: Otto Isaac, Bruchkobel; Heribert Offermanns, Grossauheim, both of Germany

[73] Assignee: Deutsche Gold- und Silber-Scheideanstalt vormals Roessler, Germany

[22] Filed: Apr. 8, 1974

[21] Appl. No.: 459,205

[30] Foreign Application Priority Data
Apr. 7, 1973   Germany............................ 2317583

[52] U.S. Cl............................ 260/617 R; 260/631.5
[51] Int. Cl.² ............................................ C07C 29/30
[58] Field of Search.......... 260/617 R, 617 A, 631.5

[56] References Cited
UNITED STATES PATENTS
2,369,163   2/1945   Milas .............................. 260/617 A FOREIGN PATENTS OR APPLICATIONS
540   1/1903   United Kingdom.............. 260/631.5

OTHER PUBLICATIONS
Simonsen, "The Terpenes," Vol. III, p. 126, (1952).

Primary Examiner—Donald G. Daus
Assistant Examiner—D. B. Springer
Attorney, Agent, or Firm—Cushman, Darby & Cushman

[57] ABSTRACT

α- Bisabolol of plant origin is purified by being treated with alkali hydroxide, alkali alcoholate, alkali carbonate, alkali bicarbonate, alkaline earth hydroxide, alkaline earth oxide or aluminium hydroxide. Preferably activated carbon is also used in the purification. Preferably the α-bisabolol is treated with pure nitrogen gas before the alkali treatment.

13 Claims, No Drawings

PROCESS FOR THE RECOVERY OF PURE ALPHA-BISABOLOL

This application if a continuation-in-part of application Ser. No. 363,163, filed May 23, 1973 and now abandoned.

α- Bisabolol is found in various plants in either the laevo rotatory or dextro rotatory form. Thus (−)α-bisabolol is a constituent of essential oils from *Cananga ordorata, Citrus bigaradia, Lavandula spica, Matricaria chamomilla, Myoporum crassifolium, Myrocarpus fastigiatus, Myrocarpus frondosus* and *Vanillosmopsis erythropappa.* ( + ) α-bisabolol is found in kinds of poplars, namely in the buds of Populus balsamifera and Populus tacamahaca.

α -bisabolol is a viscous, colorless, weakly odoriferous liquid of B.P. $_{(12\ mm)}$ 153° C. α-Bisabolol has strong, markedly olfactory fixing properties and therefore is used in cosmetics as a fixation agent for perfume (German Pat. No. 1,081,170). This firm attachment of intensely odoriferous materials to α-bisabolol, however, also prevents the recovery of pure α-bisabolol from natural essential oils by customary processes (for example, high vacuum distillation) since the α-bisabolol in the essential oils as a rule is associated with strongly odoriferous substances, which either in general cannot be separated from it or can only be very difficultly separated.

There has now been found a process for the purification of α-bisabolol arising from plants which is characterized in that bisabolol which is recovered from plant material in known manner is treated with alkali hydroxide, for example, sodium hydroxide, lithium hydroxide or potassium hydroxide; alkali alcoholates, e.g., sodium methylate, potassium methylate, sodium ethylate, potassium ethylate, sodium propylate, potassium propylate, sodium isopropylate, potassium isopropylate, sodium butylate, potassium butylate, sodium amylate, or sodium decylate; alkali carbonates, e.g., sodium carbonate or potassium carbonate; alkali bicarbonate, e.g., sodium bicarbonate or potassium bicarbonate; alkaline earth hydroxides, e.g., magnesium hydroxide, calcium hydroxide, strontium hydroxide or barium hydroxide; alkaline earth metal oxides, e.g., magnesium oxide, calcium oxide, strontium oxide or barium oxide or aluminium hydroxide. The named materials can be used in admixture with each other. Examples of such mixtures include potassium carbonate; potassium carbonate and magnesium hydroxide; potassium carbonate and magnesium oxide.

According to the process of the invention there is recovered in a very simple manner α-bisabolol of satisfactory odor. The α-bisabolol obtained has only a weak, however, pleasant odor. The process of the invention has considerable significance for the use of the bisabolol for example in cosmetics since previously the unpleasant odor due to the accompanying material has prevented a wider use of the α-bisabolol.

The α-bisabolol to be purified can be obtained from the plants mentioned in the first paragraph of the specification. The process of the invention can be used with the optically active forms of α-bisabolol (laevo or dextro rotatory form) or with the racemate.

The alkaline materials used in the invention are preferably potassium hydroxide, sodium hydroxide or lithium hydroxide and the alkaline earth hydroxides, especially calcium hydroxide and barium hydroxide as well as alkali carbonates such as potassium carbonate and sodium carbonate. Likewise, suitable for example, however, are magnesium oxide and magnesium hydroxide as well as aluminum hydroxide.

The treatment with the alkaline material according to the invention generally takes place by working on the α-bisabolol with solid alkaline material or with the alkaline material in aqueous or alcoholic solution. Any conventional alcohol can be used such as methanol, ethanol, isopropanol, propanol, butanol, etc. The α-bisabolol can be added either undiluted or in solution. As solvents for the α-bisabolol there can be added known agents. Examples are:

a. saturated aliphatic or cycloaliphatic alcohols, especially saturated aliphatic alcohols, for example such with one hydroxy group. The number of the carbon atoms can be for example between 1 to 8. The cycloaliphatic alcohols are especially of 5 to 8 carbon atoms. The aliphatic alcohols have preferably 1 to 6 carbon atoms.

b. saturated and unsaturated aliphatic ethers with 2 to 14, preferably 2 to 6 carbon atoms, which can also have an additional hydroxy group such as ethyleneglycolmonoethylether, and cycloaliphatic ethers. Among the cyclic ethers are for example suitable the saturated ethers with 5 to 8 ring atoms, preferably 5 to 6 ring atoms and one or two oxygen atoms (for example tetrahydrofuran, 1,3-dioxolane).

c. halogenated hydrocarbons, preferably of lower carbon number, which for example is between 1 to 6 such as chloroform, dichloromethane, carbon tetrachloride.

d. aliphatic and aromatic hydrocarbons. The number of the carbon atoms of the aliphatic hydrocarbons can be from 5 to 11, preferably 5 to 8 (pentane, hexane, petroleum ether). Examples of aromatic hydrocarbons are benzene, methylbenzenes, ethylbenzenes.

e. saturated aliphatic lower alkyl ester of fatty acids which may have for example 1 to 18, preferably 1 to 10 C-atoms (ethylacetate, butylacetate), saturated aliphatic ketones of 3 to 10, preferably 3 to 8 C-atoms (acetone, methyl ethyl ketone, methylisobutyl ketone).

f. solvents with a nitrogen atom as pyridine, lower aliphatic alkyl- and dialkylamines (3 to 10 C-atoms) such as diethylamine, lower dialkylamides of lower fatty acids (diethylacetamide) whereby the fatty acids contain preferably 1 to 3 carbon atoms.

g. carbon disulphide h. glacial acetic acid.

Generally there is employed crude bisabolol recovered from plants in known manner. The α-bisabolol for example can come from the essential oils of rutaces (for example *Citrus aurantium* or *Citrus bigaradia*), legumes (for example, *Myrocarpus* types), composites (for example, *Matricaria chamomilla* or *Vanillosmopsis erythropappa*), salicaces, (for example Populus types), myoporaces (for example *Myoporus crassifolium*), annonaces (for example *Cananga odorata* ), labiates (for example *Lavandula spica*), pinaces (for example *Picea ajanensis*), cupressaces (for example, *Fokienia hodginsii*), umbellifers (for example, *Libanotis transcaucasica*) or malvaces (for example *Gossypium hirsutine*). The α-bisabolol (crude bisabolol) can be obtained from these essential oils for example by steam distillation, fractional distillation or chromatography (for example on aluminum oxide; see E. Gildemeister, Fr. Hoffmann "Die ätherischen Öle" Vol. b, 4th edition, Academie Verlag Berlin (1962) pages 245, et seq.)

It is suitable, at least in the starting stage of the action, to thoroughly mix the α-bisabolol and the solid alkaline material, for example by stirring or shaking.

The treatment can take place within a temperature range of 0° to 150° C. Suitably it takes place at a temperature between 20° and 100° C., preferably between 20° and 50° C. The time of treatment depends on the type of accompanying substances and is dependent on the temperature. It can be ended immediately after the alkali addition. As a rule the treatment is completed within 24 hours. However, it can also use a longer period of time.

The alkaline materials of the invention are generally used in an amount between 5 and 100% of the weight of the bisabolol. The alkaline material can be added as such in undiluted form or in the form of solutions. As solutions there can be employed aqueous solutions, alcoholic solutions or mixtures off the agents, wherein generally the concentration of the alkaline materials of the invention is between 0.5 and 50%. In most cases there is used a 5 to 20% solution. The concentration can be varied even more widely.

As the alcoholic solvent there can be used basically all alcohols which can be separated by distillation from the α-bisabolol and do not form azeotropic mixtures with the bisabolol. Especially there can be used alcohols which boil at normal pressure (760 mm) between 50° and 210° C. Examples include aliphatic alcohols, e.g., alkanols, especially those having 1 to 8 carbon atoms, preferably 1 to 4 carbon atoms, e.g., methyl alcohol, ethyl alcohol, propyl alcohol, isopropyl alcohol, butyl alcohol, sec. butyl alcohol, amyl alcohol, hexyl alcohol, octyl alcohol, isooctyl alcohol or 2-ethylhexyl alcohol, cycloaliphatic alcohols such as cyclopentanol and cyclohexanol and lower phenyl alcohols such as benzyl alcohol.

Alkali alcoholates are preferably added as solutions wherein the above named alcohols are employed.

After the treatment the alkali is separated off, for example, by filtration, centrifuging or in a separatory funnel. In the treatment with alkali solutions it is suitable subsequently to work the bisabolol phase with alkali free water and to dry.

By too strong mixing of the bisabolol or bisabolol solutions with the alkaline materials of the invention or the solutions emulsion formation can be produced. In such cases generally by less intensive mixing the emulsion formation is repressed or avoided. However, customary materials can also be added which prevent or inhibit emulsion formation (for example known silicone-antifoaming agents, e.g., polydimethyl siloxane oils).

The treatment of α-bisabolol according to the invention can be combined with a carbon treatment. It is, of course, known that natural materials can be purified by adsorption on activated carbon. In case of α-bisabolol, however, by addition of higher concentrations of activated carbon to a crude bisabolol either in the cold or in the heat, there is successfully removed the odoriferous, irritating substances.

The combination of an alkali treatment with an activated carbon treatment has the advantage that still further odoriferous non-relevant accompanying materials are removed from the crude bisabolol and accordingly, for example, further make simple a subsequent distillation. Thereby the activated carbon treatment can take place simultaneously with or after the alkaline treatment of the invention. The simultaneous treatment has proven especially suitable. For example, there can be used 1 to 200%, preferably 10 to 100% of activated carbon, based on the bisabolol weight.

First of all by the process of the invention odoriferous, disturbing accompanying materials are removed which chiefly are present in small amounts. In case a crude bisabolol is added hereby, this contains primarly still other impurities from which the α-bisabolol can be separated in known manner in connection with the treatment of the invention, for example, by high vacuum distillation or chromatography. The high vacuum distillation can be carried out, for example, by batch distillation or by use of evaporators which guarantee a nice evaporation and small pressure loss. These types of evaporators for example, are all film evaporators with mechanically produced films (for example Sambay evaporators) or falling film evaporators.

In the high vacuum distillation distillation must be over a column. As columns there can be considered those which guarantee the slightest possible pressure loss and the heat radiation reduced to a minimum. Suitable are Vigreux columns, plate columns, and preferably packed columns with Raschig rings, helices of glass or metal or packing.

The chromatographic separation is carried out in known manner. As adsorption agents there can be used, for example, silica gels as well as acid, neutral or basic aluminum oxide. Running media, for example, are benzene, petroleum ether, chloroform, ethyl acetate or mixtures thereof. The chromatographic purification can be carried out, for example, in the manner described in the Deutschen Apotheker-Zeitung 108 (1968) page 293 or in Collection Czech. Chem. Commun. 16 (1951), page 676.

It is understood that it is also possible from the first to add an almost pure α-bisabolol, which still only contains odoriferously disturbing accompanying materials. In such cases, in a given case no distillation or further purification is necessary after the treatment according to the invention.

The effect which is produced by the individual purification steps is illustrated by the following Table.

TABLE

Recovery of pure (−) α-bisabolol from the essential oil of *Vanillosmopsis erythropappa*

| Step | Product | Bisabolol content |
|---|---|---|
| 1 | essential oil (crude bisabolol) | 87% |
| 2 | after alkali treatment | 95% |
| 3 | after alkali and activated carbon treatment | 97.4% |
| 4 | after high vacuum distillation | 99.5% |

Unless otherwise indicated all parts and percentages are by weight.

EXAMPLE 1

100 grams of unpleasantly smelling essential oil from *Vanillosmopsis erythropappa* (87% bisabolol) were dissolved in 1000 ml petroleum ether. The solution was shaken in a separatory funnel with 500 ml of 5% aqueous soda lye.

After 24 hours the alkaline phase was separated. The petroleum ether phase was washed several times with water, dried over sodium sulfate and the petroleum ether distilled off. The thus treated bisabolol was distilled over a vacuum jacket packed column in a high vacuum at 0.1 mmHg. The weakly aromatic smelling to odorless portion passing over at 114° to 115°C. was collected. Yield: 77 grams, 99.5% (−) α-bisabolol.

EXAMPLE 2

100 grams of strongly balsamic smelling essential oil from *Populus tacamahaca* (73.5% bisabolol) were dissolved in 1000 ml of petroleum ether. The solution was shaken for 30 minutes with 50 grams potassium carbonate. Subsequently the residue was filtered off and the petroleum ether distilled off from the filtrate.

The thus treated bisabolol was distilled in high vacuum at 0.1 mmHg. The weakly aromatic smelling to odorless portion going over at 114° to 115°C. was collected. Yield: 62 grams of 99% (+) α-bisabolol.

EXAMPLE 3

100 grams of unpleasantly smelling essential oil from *Vanillosmopsis erythropappa* (87% bisabolol) were dissolved in 1000 ml of petrolum ether. The solution was shaken for 1 hour with a mixture of 25 grams of potassium carbonate and 25 grams of activated carbon. Subsequently the residue was filtered off and the petroleum ether distilled off from the filtrate.

The residue was distilled in a high vacuum at 0.1 mmHG. The weakly aromatic smelling to odorless portion going over at 112° to 114°C. was collected. Yield: 75 grams of 99.5% (−) α-bisabolol.

It has further been found especially advantageous to gas the impure α-bisabolol with nitrogen prior to the treatment with alkali.

The gassing with nitrogen can take place either at room temperature or with heating. Thus, temperatures between room temperature (about 20° C). and 100° C. can be used, preferably between 30° and 60°C.

It is recommended to stir the bisabolol or to keep it in motion by other customary methods during the gassing with nitrogen. The nitrogen used should be pure and free of oxygen and, if necessary, can be purified by conventional techniques prior to use. The time of nitrogen gassing, for example, can be between 1 and 5 hours. This time can be varied.

EXAMPLE 4

1000 grams of unpleasantly smelling essential oil from *Vanillosmopsis erythropappa* (87% bisabolol) were distilled in a high vacuum at 0.4 mm Hg.

The portion passing over at 119 to 125° C. and still smelling strongly was collected (597 grams containing 98.5% bisabolol), heated to 60° C. with nitrogen (that had been passed through a pyrogallol solution according to Houben-Weyl I/2 page 332 to remove any oxygen present) from below by means of a glass frit.

The gassed bisabolol was treated with 25 grams of activated carbon and 10 grams of potassium carbonate and stirred for 2 hours at 60° C. The mixture was filtered warm through a Seitz-AW-filter layer.

Yield 530 grams of 99.8% α-bisabolol as a colorless and odorless oil.

What is claimed is:

1. A process for the purification of α-bisabolol originating from plants comprising the step of subjecting the impure α-bisabolol still containing odoriferous impurities to alkali hydroxide, alkali alkanoate of 1 to 8 carbon atoms, alkali cyclopentanolate, alkali cyclohexanolate, alkali benzyl alcoholate, alkali carbonate, alkali bicarbonate, alkaline earth hydroxide, alkaline earth oxide or aluminum hydroxide at a temperature of 20° to 60°C. under alkaline conditions and recovering the purified bisabolol.

2. A process according to claim 1 including the step of employing activated carbon simultaneously with said alkaline treatment to remove impurities from the α-bisabolol.

3. A process according to claim 1 including the step of purifying the α-bisabolol chromatographically after said alkaline treatment.

4. A process according to claim 3 also including the step of employing activated carbon prior to the chromatographic purification to remove impurities from the α-bisabolol.

5. A process according to claim 1, including a high vacuum distillation to recover pure bisabolol.

6. A process according to claim 5 including the step of employing activated carbon to remove impurities from the α-bisabolol prior to the distillation.

7. A process according to claim 5 wherein the vacuum treatment is at 0.1 mm Hg.

8. A process according to claim 1, wherein the temperature is 20° to 50°C.

9. A process according to claim 1 including the step of employing activated carbon after said alkali treatment to remove impurities from the α-bisabolol.

10. A process for the purification of α-bisabolol originating from plants comprising gassing the impure α-bisabolol still containing odoriferous impurities with oxygen free nitrogen gas at a temperature up to 100°C., and thereafter comprising the step of subjecting the αbisabolol containing impurities to alkali hydroxide, alkali alkanoate of 1 to 8 carbon atoms alkali cyclopentanoate, alkali cyclohexanolate, alkali benzyl alcoholate, alkali carbonate, alkali bicarbonate, alkaline earth hydroxide, alkaline earth oxide or aluminum hydroxide at a temperature of 20° to 60°C. under alkaline conditions and recovering the purified bisabolol.

11. A process according to claim 10 wherein the nitrogen gassing is at 30° to 60°C.

12. A process according to claim 10 comprising subjecting the impure bisabolol to a high vacuum distillation prior to the gassing with nitrogen.

13. A process according to claim 10 wherein the nitrogen gassing is for 1 to 5 hours.

* * * * *